(12) United States Patent
Weil et al.

(10) Patent No.: US 6,369,114 B1
(45) Date of Patent: Apr. 9, 2002

(54) ADMINISTRATION OF AN $\alpha_2$-ADRENERGIC RECEPTOR AGONIST TO ENHANCE CARDIOPULMONARY RESUSCITATION

(75) Inventors: Max Harry Weil, Northbrook, IL (US); Wanchun Tang, Palm Desert; Jose Bisera, Camarillo, both of CA (US)

(73) Assignee: Institute of Critical Care Medicine, Palm Springs, CA (US)

( * ) Notice: Subject to any disclaimer, the term of this patent is extended or adjusted under 35 U.S.C. 154(b) by 0 days.

(21) Appl. No.: 09/451,468

(22) Filed: Nov. 30, 1999

(51) Int. Cl.$^7$ .................. A01N 43/46; A01N 33/02; A61K 31/55; A61K 31/135
(52) U.S. Cl. .............. 514/653; 514/821; 514/854; 514/215; 514/81
(58) Field of Search .................. 514/215, 81, 653, 514/821, 854

(56) References Cited

U.S. PATENT DOCUMENTS

| | | |
|---|---|---|
| 4,296,119 A | 10/1981 | Wurtman .................... 514/419 |
| 4,683,229 A | 7/1987 | Demarinis et al. ........... 514/213 |
| 4,693,243 A | 9/1987 | Buras .................... 128/207.15 |
| 4,904,472 A | 2/1990 | Belardinelli et al. ........ 514/263 |
| 4,980,379 A | 12/1990 | Belardinelli et al. ........ 514/821 |
| 5,204,116 A | 4/1993 | Edgren et al. .............. 428/473 |
| 5,216,032 A | 6/1993 | Manning .................... 514/718 |
| 5,588,422 A | 12/1996 | Lurie et al. ............ 128/200.24 |

OTHER PUBLICATIONS

Beers and Berkow, eds. The Merck Manual of Diagnosis and Therapy, Seventeenth Edition. Merck Research Laboratories, Whitehouse Station, N.J. 1999, pp. 1740–1753.*

Brown et al. (1992), "A Comparison of Standard–Dose and High–Dose Epinephrine in Cardiac Arrest Outside the Hospital," *N. Engl. J. Med.* 327:1051–1055.

Cantineau et al. (1994), "Effect of Epinephrine on End–Tidal Carbon Dioxide Pressure During Prehospital Cardiopulmonary Resuscitation," *Am. J. Emerg. Med.* 12:267–270.

C. Johnson (1992), "Endotracheal Drug Delivery," *Pediatric Emergency Care* 8(2):94–97.

Otto (1986), "Cardiovascular Pharmacology II: the Use of Catecholamines, Pressor Agents, Digitalis, and Corticosteroids in CPR and Emergency Cardiac Care," *Circulation* 74 (4):80–85.

Stiell et al. (1992), "High–Dose Epinephrine in Adult Cardiac Arrest," *N. Engl. J. Med.* 327 (15):1045–1050.

Tang et al. (1991), "Pulmonary Ventilation/Perfusion Defects Induced by Epinephrine During Cardiopulmonary Resuscitation," *Circulation* 84:2101–2107.

Tang et al. (1995), "Epinephrine Increases the Severity of Postresuscitation Myocardial Dysfunction," *Circulation* 92:3089–3093.

* cited by examiner

*Primary Examiner*—Prema Mertz
*Assistant Examiner*—Joseph F. Murphy
(74) *Attorney, Agent, or Firm*—Dianne E. Reed; J. Elin Hartrum; Reed & Associates (57) ABSTRACT

Methods, formulations and kits are described for resuscitating a patient suffering from cardiac arrest, for enhancing the efficacy of cardiopulmonary resuscitation, for treating post-resuscitation hypotension, and for reducing the incidence of ventricular arrhythmias and myocardial dysfunction in a patient following cardiopulmonary resuscitation. Prior methods and agents often cause inotropic or chronotropic effects, which can lead to undesirable post-resuscitation myocardial dysfunction. The invention comprises administering a therapeutically effective amount of an $\alpha_2$-receptor agonist that does not cross the blood-brain barrier, such as $\alpha$-methylnorepinephrine, to enhance cardiopulmonary resuscitation.

43 Claims, 7 Drawing Sheets

FIG 6. EJECTION FRACTION

ADMINISTRATION OF AN $\alpha_2$-ADRENERGIC RECEPTOR AGONIST TO ENHANCE CARDIOPULMONARY RESUSCITATION

TECHNICAL FIELD

The present invention relates generally to cardiopulmonary resuscitation, i.e., restoration of a patient's respiration and blood circulation following cardiac arrest. More particularly, the invention relates to a method for enhancing cardiopulmonary resuscitation by systemic administration of an $\alpha_2$-adrenergic receptor agonist. The invention finds utility in the areas of pharmacology, cardiology and general medicine.

BACKGROUND

In cardiac arrest, a patient's heart ceases its normal pumping action and frequently devolves into ventricular fibrillation. Without restoration of circulation, death from anoxia is rapid. Cardiac arrest is a major cause of death and can arise from a variety of circumstances, including heart disease, electric shock and other trauma, suffocation, and the like. To improve the likelihood of patient survival and reduce the likelihood of damage to the brain and heart resulting from oxygen deprivation, it is essential that a patient's respiration and blood circulation be restored as soon as possible. A number of resuscitation techniques have been developed with the aforementioned objectives in mind.

Generally, cardiopulmonary resuscitation (CPR) techniques are used that rely on external chest compression. Standardized cardiopulmonary restoration (CPR) techniques are described in "Guidelines for CPR and Emergency Cardiac Care," *J. Am. Med. Assoc.* 268:2205–2211 (1992), which sets out in detail the recommended procedures for administration of drugs and physical intervention in CPR. Manual CPR techniques rely on the application of a downward force on the patient's chest in order to force blood from the heart and expel air from the lungs. Ventilation by either mouth-to-mouth or mechanical techniques is performed concurrently with chest compression in order to force air back into the patient's lungs. Such manual CPR techniques, however, rely in large part on the natural elasticity of the chest in order to actively draw venous blood back into the heart, which is generally inefficient. Long-term survival in cardiac arrest patients who have undergone manual CPR is usually below 10%.

An improved CPR method is referred to as active compression/decompression (ACD) CPR. The ACD CPR technique results in improved blood circulation through the heart and ventilation of the patient's lungs when compared to standard CPR techniques. ACD CPR combines external cardiac compression with active expansion of the patient's chest after each compression in order to lower intrathoracic pressure and facilitate refilling of the heart. ACD CPR is generally performed with a commercially available device such as the CardioPump, available from Ambu International A/S (Copenhagen). Such devices involve use of a vacuum cup that is applied to the anterior chest wall of the patient, and is used to enable active expansion of the patient's chest after each compression, to expand the thorax and heart.

Another alternative procedure for inducing blood transport and lung ventilation is known as "mast trouser" ventilation, which is performed by placing the patient's lower extremities in inflatable trousers, which are then inflated to force blood into the thorax and heart. An additional technique involves "vest" cardiovascular resuscitation in which the patient is placed in a vest or the like that is capable of pressurizing the chest to expel blood from the thorax.

ACD CPR and other enhanced CPR methods have been established to improve the chances for patient survival relative to conventional CPR. However, it would be desirable if the chances of patient survival could be increased even further.

To this end, advanced cardiac life support (ACLS) techniques have been developed. Such techniques typically include the intravenous or endotracheal administration of fluids and pharmacological agents during performance of CPR. A review of the pharmacological agents that are generally administered in conjunction with cardiopulmonary resuscitation can be found in Otto (December 1986), *Cir.* 74 (supplement IV), IV-80–85.

Rapid restoration of coronary perfusion and therefore myocardial blood flow is the overriding determinant of the success of CPR during cardiac arrest. It provides a rationale for the widespread use of adrenergic vasopressor agents and especially epinephrine. *J. Am. Med. Assoc.* 268:2205–2211 (1992), cited supra. Increases in arterial resistance enhance aortic diastolic pressure, coronary perfusion pressure and myocardial blood flow during either closed-chest precordial compression, as described above, or open chest cardiac massage. The success of electrical defibrillation is contingent upon restoring threshold levels of myocardial blood flow after prolonged cardiac arrest. Duggal et al. (1993), "Regional Blood Flow During Closed Chest Cardiac Resuscitation in Rats," *J. Appl. Physiol.* 74:147–152.

Epinephrine has been the preferred adrenergic agent for the treatment of human cardiac arrest for almost 30 years. When vasopressor agents with P-adrenergic actions, like epinephrine, are administered to enhance coronary perfusion during CPR, however, $\beta$-adrenergic effects simultaneously increase myocardial oxygen requirements. Ditchey et al. (1988), "Failure of Epinephrine to Improve the Balance Between Myocardial Oxygen Supply and Demand During Closed-Chest Resuscitation in Dogs," *Circulation* 78:382–389; Ditchey et al. (1989), "Phenylephrine plus Propranolol Improves Myocardial Oxygenation During CPR," *Circulation* 80:492–494. Consequently, epinephrine can increase the severity of post-resuscitation myocardial dysfunction and decrease the rate of survival. Tang et al. (1993), "Progressive Myocardial Dysfunction After Cardiac Resuscitation," *Crit. Care Med.* 21:1046–1050; Tang et al. (1995), "Epinephrine Increases the Severity of Post-Resuscitation Myocardial Dysfunction," *Circulation* 92:3089–3093.

The $\beta$-adrenergic effects of epinephrine also alter the distribution of pulmonary blood flow and thereby produce ventilation/perfusion abnormalities such that they induce an increase in the arterial partial pressure of carbon dioxide ($PCO_2$) and a decrease in the arterial partial pressure of oxygen ($PO_2$). In one study, end tidal $CO_2$ ($ETCO_2$) was found to decrease by 50% immediately following administration of epinephrine both under physiological conditions of spontaneous circulation and during CPR. Tang et al. (1991), "Pulmonary Ventilation/Perfusion Defects Induced by Epinephrine During Cardiopulmonary Resuscitation," *Circulation* 84:2101–2107; Cantineau et al. (1994), "Effect of Epinephrine on End-Tidal Carbon Dioxide Pressure During Prehospital Cardiopulmonary Resuscitation," *Am. J. Emerg. Med.* 12:267–270. The $\beta$-adrenergic effects of epinephrine also increase the risk of re-entrant and ectopic ventricular dysrhythmias after successful resuscitation, issues that may be of even greater importance when high doses of epinephrine are administered. Brown et al. (1992), "A Comparison of Standard-Dose and High-Dose Epinephrine in Cardiac Arrest Outside the Hospital," *N. Engl. J. Med.*

327:1051–1055; Stiell et al. (1992), "High-Dose Epinephrine in Adult Cardiac Arrest," *N. Engl. J. Med.* 327:1045–1050.

Predominant $\alpha_1$-adrenergic agents such as phenylephrine and methoxamine were found to be as effective as epinephrine for restoring spontaneous circulation. Tang et al. (1991), supra; Tang et al. (1995), supra. However, the inotropic effects of these agents increase myocardial oxygen consumption during cardiac arrest and therefore increase the severity of post-resuscitation myocardial dysfunction. Rapid desensitization of presynaptic $\alpha_1$-adrenergic receptors during ischemia, especially when the duration of untreated cardiac arrest is prolonged, reduces the potency the $\alpha_1$-adrenergic agent administered.

It would therefore be desirable to provide an improved method for cardiopulmonary resuscitation wherein coronary perfusion pressure and therefore myocardial blood flow is rapidly restored, the incidence of post-resuscitation ventricular arrhythmias is minimized, the severity of post-resuscitation myocardial dysfunction is decreased, and the overall likelihood of patient survival is increased.

SUMMARY OF THE INVENTION

Accordingly, it is a primary object of the invention to address the above-described need in the art by providing a method for enhancing the efficacy of cardiopulmonary resuscitation and minimizing post-resuscitation myocardial dysfunction.

It is another object of the invention to provide such a method by administering an $\alpha_2$-adrenergic receptor agonist to a patient following cardiac arrest, during or subsequent to performing cardiopulmonary resuscitation procedures.

It is another object of the invention to provide such a method wherein the active agent administered is a selective $\alpha_2$-adrenergic receptor agonist.

It is an additional object of the invention to provide such a method wherein the active agent administered is α-methylnorepinephrine.

It is a further object of the invention to provide a kit for conducting the therapeutic methods described and claimed herein.

Additional objects, advantages and novel features of the invention will be set forth in part in the description which follows, and in part will become apparent to those skilled in the art upon examination of the following, or may be learned by practice of the invention.

In one embodiment, a method is provided for enhancing the efficacy of cardiopulmonary resuscitation, i.e., for increasing the likelihood of patient survival, decreasing the severity of post-resuscitation myocardial dysfunction, and reducing the incidence of post-resuscitation ventricular arrhythmias. The method comprises administering an $\alpha_2$-adrenergic receptor agonist to a patient following cardiac arrest, in combination with conventional or enhanced cardiopulmonary resuscitation procedures. The preferred active agents are $\alpha_2$-adrenergic receptor agonists that do not cross the blood-brain barrier, and particularly preferred active agents within this group are selective $\alpha_2$-adrenergic receptor agonists such as α-methylnorepinephrine. These active agents cause vasoconstriction and therefore raise aortic pressure to restore coronary perfusion and thereby myocardial blood flow without the detriment of inotropic or chronotropic actions during and following cardiopulmonary resuscitation.

In another embodiment, a kit is provided for carrying out the aforementioned therapeutic method, wherein the kit comprises: a pharmaceutical formulation comprising an $\alpha_2$-adrenergic receptor agonist as described herein; a closed container housing the formulation; a means for administering the formulation to a patient; and instructions for administering the formulation to enhance the efficacy of cardiopulmonary resuscitation following cardiac arrest.

DETAILED DESCRIPTION OF THE INVENTION

It is to be understood that unless otherwise indicated this invention is not limited to specific cardiopulmonary resuscitation procedures, pharmaceutical formulations or active agents, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to use of "an $\alpha_2$-adrenergic receptor agonist" includes two or more such receptor agonists, reference to "a carrier" as in a pharmaceutical formulation containing "a carrier" includes combinations of two or more different carriers, and the like.

In this specification and in the claims which follow, reference will be made to a number of terms which shall be defined to have the following meanings:

The term "cardiac arrest" refers to a physiological state associated with loss of effective heart function and effective blood circulation. Specific conditions associated with cardiac arrest and treatable using the methods of the present invention include ventricular fibrillation, characterized by rapid contractions and twitching of the heart muscle; asystole, characterized by the substantial absence of contractions of the heart; and pulseless electrical activity (PEA), characterized by the persistence of electrical activity in the heart without associated mechanical contractions.

The term "cardiac output" as used herein is given its standard meaning, that is, cardiac output is the volume of blood being pumped by the heart per unit time.

The term "cardiac index" as used herein is given its standard meaning, that is, the cardiac index is cardiac output divided by the weight of the animal. An alternative usage of the term "cardiac index" normalizes the cardiac output to the surface area of the body of an animal; these usages may be readily related by the common practice of estimating surface area from the weight of the animal, often with the use of known relationships between body weight and surface area (e.g., see *Medical Physiology*, 13$^{th}$ Edition, page 1246, edited by V. Mountcastle, published by C. V. Mosby, 1974).

The term "stroke volume" as used herein is given its standard meaning, that is, the volume of blood ejected from a ventricle per beat.

The term "ejection fraction" as used herein is given its standard meaning, that is, the fraction of the blood ejected from a ventricle during each beat, compared with the volume of blood present at the beginning of a beat.

The term "resuscitation" as in "cardiopulmonary resuscitation" refers to restoration of coronary perfusion in a patient in cardiac arrest. By "enhancing" cardiopulmonary resuscitation is meant enhancing the efficacy of the CPR process, in general, so that the chances of a patient's survival are improved; the term also refers to preventing, minimizing or treating myocardial dysfunction and/or reducing the incidence of ventricular arrhythmias in a patient following cardiopulmonary resuscitation.

By the term "effective amount" of a compound as provided herein is meant at least a sufficient amount of the compound to provide the desired effect, i.e., restoration of coronary perfusion and myocardial blood flow. A "therapeutically effective amount" of an active agent herein, used to treat a mammalian individual during and/or following cardiac arrest, is an amount that is nontoxic but sufficient to provide the desired effect. The exact amount required will vary from subject to subject, depending on the species, age, and general condition of the subject, the particular active agent, mode of administration, and the like.

By "pharmaceutically acceptable carrier" in the pharmaceutical formulations herein is meant a material that is not biologically or otherwise undesirable, i.e., the material may be administered to an individual along with the active agent without causing any undesirable biological effects or interacting in a deleterious manner with any of the other components of the pharmaceutical formulation in which it is contained.

The active agent administered in the method of the present invention is an $\alpha_2$-adrenergic receptor agonist, also referred to herein as an "$\alpha_2$-receptor agonist" or simply as an "$\alpha_2$ agonist." As will be appreciated by those skilled in the art, a receptor "agonist" is a drug that binds to a particular physiological receptor and mimic the effects of the endogenous regulatory compounds (see, e.g., Goodman & Gilman's *The Pharmacological Basis of Therapeutics*, Ninth Edition, Eds. Hardman et al. (New York: McGraw-Hill, 1996)). As is also well known, adrenergic receptors have been classified into five groups: $\alpha_1$, $\alpha_2$, $\beta_1$, $\beta_2$ and $\beta_3$. The designations $\alpha$ and $\beta$ refer to those receptors on smooth muscle where catecholamines produce excitatory and inhibitory responses, respectively. Like the $\beta$-adrenergic receptors, the $\alpha$-adrenergic receptors are heterogeneous, and classified as either $\alpha_1$ or $\alpha_2$ receptors.

The preferred $\alpha_2$ agonists useful in the method of the invention are those $\alpha_2$ agonists that do not cross the "blood-brain barrier" (BBB), the recognized permeability barrier to the passive diffusion of substances from the bloodstream into various regions of the central nervous system (CNS). Agents that do not cross the BBB, when present in the blood of a patient, are substantially absent from the CNS, being either not present, or present in only a small fraction of the amount present in the blood. Thus, administration of the preferred $\alpha_2$ agonists, i.e., $\alpha_2$ agonists that do not cross the BBB, result in substantially none of the $\alpha_2$ agonist passing from the bloodstream and entering the CNS. Particularly preferred $\alpha_2$ agonists useful herein are selective $\alpha_2$-receptor agonists, including, but not limited to α-methylnorepinephrine (α-(1-aminoethyl),3,4-dihydroxybenzyl alcohol; also referred to as "nordefrin")

α-Methylnorepinephrine

Such agents vasoconstrict and therefore raise aortic pressure to restore coronary perfusion and thereby myocardial blood flow without the detriment of inotropic or chronotropic actions during and following cardiopulmonary resuscitation. Thus, it has been discovered that $\alpha_2$ agonists that produce vasoconstriction, without inotropic or chronotropic effects, and agents that do not cross the BBB are useful agents for cardiopulmonary resuscitation.

Unlike α-methylnorepinephrine and other preferred $\alpha_2$ agonists, many other $\alpha_2$ agonists cross the blood-brain barrier and act on the brain stem such as to cause vasodilation, as in the case of clonidine, together with reduced arterial blood pressure. Non-preferred $\alpha_2$ agonists that cross the BBB adversely effect myocardial blood flow produced by chest compression and therefore reduce the likelihood of successful resuscitation. In addition, the $\alpha_2$ agonist acting on the central nervous system produces negative inotropic and chronotropic actions. Accordingly, use of the selective $\alpha_2$ agents which do not cross the blood brain barrier as proposed herein represents an important and heretofore unsuggested advance in the art.

For α-methylnorepinephrine and other amine-containing active agents, the compounds will typically although not necessarily be administered as an aqueous solution; they may be provided in aqueous solution, or in the form of an acid addition salt, which may be prepared from the free base using conventional means, involving reaction with a suitable acid. The active agent may be provided in the form of a pharmaceutically acceptable salt, ester, amide, prodrug, derivative, or the like. The agents may be stored in either dry or liquid form before use.

Typically, the base form of the compound is dissolved in a solvent such as methanol or ethanol and the acid is added. The resulting salt either precipitates or may be brought out of solution by addition of a less polar solvent. Suitable acids for preparing acid addition salts include both inorganic acids, e.g., hydrochloric acid, hydrobromic acid, sulfuric acid, nitric acid, phosphoric acid, and the like, as well as organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, etc. An acid addition salt may be reconverted to the free base by treatment with a suitable base.

The compounds of the invention may be modified in other ways as well, as will be appreciated by those skilled in the art.

The active agent is generally administered to the patient in a pharmaceutical formulation comprising a pharmaceutically acceptable carrier suitable for the selected mode of administration. See *Remington: The Science and Practice of Pharmacy,* 19th Ed. (Easton, Pa.: Mack Publishing Co., 1995), which discloses typical carriers and conventional methods of preparing pharmaceutical compositions that may be used as described or modified to prepare pharmaceutical formulations containing the compounds of the invention.

The active agent may be administered parenterally, endotracheally, or via an implanted reservoir. The term "parenteral" as used herein is intended to include subcutaneous, intravenous, and intramuscular injection, with intravenous administration preferred herein, and most preferred being administration of a single bolus of the active agent. The amount of active agent administered will, as noted earlier herein, be dependent on the subject being treated, the subject's weight, the mode of administration and the judgment of the prescribing physician. Generally, however, the dosage will be in the range of approximately 10 $\mu$g/kg to 1.0 mg/kg, more preferably in the range of approximately 20 $\mu$g/kg to 500 $\mu$g/kg, most preferably in the range of approximately 50 $\mu$g/kg to 200 $\mu$g/kg.

Parenteral administration is generally characterized by injection. Injectable formulations can be prepared in conventional forms, either as liquid solutions or suspensions, as solid forms suitable for solution or suspension in liquid prior to injection, or as emulsions. Preferably, sterile injectable suspensions are formulated according to techniques known in the art using suitable dispersing or wetting agents and suspending agents. Sterile injectable solutions or suspensions will generally be formulated in a nontoxic parenterally acceptable diluent or solvent. Acceptable vehicles and solvents that may be employed include, but are not limited to, water, Ringer's solution and isotonic sodium chloride solution. In addition, sterile, fixed oils are conventionally employed as a solvent or suspending medium.

Endotracheal administration is particularly suitable if an endotracheal tube has been placed in order to enhance lung ventilation and intravenous access is not immediately available. Devices and methods suitable for endotracheal administration of active agents will be known to those skilled in the art and are described in the pertinent texts and literature; see, for example, U.S. Pat. No. 4,693,243 and Johnson (1992), "Endotracheal Drug Delivery," *Pediatric Emergency Care* 8(2):94–97. In general, drugs may be administered through an endotracheal tube after dilution in approximately 10 ml of saline, dextrose solution, or water. The drug-containing solution may be placed in a long catheter situated inside the endotracheal tube, with the tip of the catheter extending beyond the tip of the endotracheal tube, and the drug solution injected from the tip of the catheter.

The active agent may be administered with one or more additional active agents, either additional $\alpha_2$-adrenergic agonists or other types of active agents, including, but not limited to: class I antiarrhythmic agents, such as amiodarone, quinidine, procainamide, disopyramide, mixelitine, lidocaine, tocainide, phenytoin, flecainide, moricizine, and propafenone; class II antiarrhythmic agents, such as propanolol, esmolol, and sotalol (which is also a class III agent); class III antiarrhythmic agents, such as bretylium and ibutilide; and class IV antiarrhythmic agents, such as verapamil, diltiazem, and bepridil; and other antiarrhymic agents, such as digoxin, edrophonium, adenosine, magnesium and potassium.

In one embodiment, then, the $\alpha_2$-adrenergic agonist is administered in combination with conventional (manual or mechanically enhanced) CPR in order to resuscitate a patient suffering from cardiac arrest. That is, a patient is resuscitated by (a) actively inducing venous blood transport into the heart and arterial blood transport from the heart, (b) ventilating the patient's lungs, and (c) administering an active agent as provided herein, i.e., the $\alpha_2$-adrenergic agonist. The active agent should be administered to the patient concurrently with or as soon as possible after initiation of the CPR procedure, preferably within about 60 minutes of initiating CPR, more preferably within about 10 minutes of initiating CPR. The active agent will preferably be administered in a bolus injection, which may be repeated about every three to 5 minutes if necessary. The CPR method used may be manual, ACD CPR, as described earlier herein, or an alternative method of reestablishing blood flow by mechanical means.

In another embodiment, an electrical defibrillatory shock is applied to a patient in cardiac arrest, and the $\alpha_2$-adrenergic agonist is administered to the patient prior to, during and/or subsequent to electrical defibrillation. Electrical defibrillation is conducted using conventional means, via endocardial and epicardial electrode placement via transthoracic pacing electrodes. The method of the invention substantially improves the likelihood that electrical defibrillation will be successful, insofar as administration of an $\alpha_2$-receptor agonist in combination with electrical defibrillation facilitates rapid restoration of myocardial blood flow.

In another embodiment, an $\alpha_2$-receptor agonist is administered to a patient in order to treat or prevent the incidence of post-resuscitation ventricular arrhythmias, myocardial dysfunction or hypotension. For example, the active agent, with or without other agents, may be administered as a continuous infusion in order to treat post-resuscitation hypotension.

The invention also encompasses a kit for physicians to use in carrying out the present method. The kit contains at least the following: a pharmaceutical formulation comprising an $\alpha_2$-receptor agonist that does not cross the BBB; a device for administering the formulation (e.g., a syringe); a container, preferably sealed, for housing the formulation and device during storage and prior to use; and instructions for carrying out administration of the formulation in a manner effective to enhance cardiopulmonary resuscitation following cardiac arrest. The formulation will generally contain the active agent in unit dosage form. The kit may also contain multiple formulations of different dosages of the same agent, or multiple formulations of different active agents. The instructions may be in written and/or pictograph form.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, journal articles and other reference cited herein are incorporated by reference in their entireties.

EXPERIMENTAL

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

Sprague-Dawley rats (450–570 g) were fasted overnight except for free access to water. The animals were anesthetized by intraperitoneal injection of 45 mg/kg pentobarbital sodium supplemented with additional doses of 10 mg/kg at hourly intervals, except that no pentobarbital was administered for 30 minutes before induction of cardiac arrest. The trachea was orally intubated with a 14-gauge cannula (Quick-Cath, Vicra division, Travenol Laboratory) mounted on a blunt needle with a 145° angled tip. For measurement of the partial pressure of carbon dioxide in the endotracheum ($P_{ET}CO_2$), the respiratory gas was sampled through a side manifold interposed between the tracheal cannula and the respirator. The $PCO_2$ was measured with a side-stream infrared $CO_2$ analyzer (model 200, Instrumentation Laboratories). For measurement of left ventricular pressure, and both $dP/dt_{40}$ (the rate of left ventricular pressure increase measured at a left ventricular pressure of 40 mm Hg, an indicator of isovolemic contractility) and negative dP/dt (the rate of left ventricular pressure decline, a measure of myocardial relaxation), a Teflon catheter (UTX 022; internal diameter, 0.6 mm; outer diameter, 0.97 mm; length 8 cm; Becton Dickinson) was advanced into the left ventricle from the right carotid artery. Through the left external jugular vein, an 18-gauge polyethylene catheter (CPMS-401J-Fa, Cook) was advanced through the superior vena cava into the right ventricle. Guided by pressure monitoring, the catheter was slowly withdrawn into the right atrium. Right atrial pressure was measured with reference to the midchest with a high-sensitivity transducer (P-23-9b, Spectramed). This catheter was also used to sample blood from the right atrium. Through the right external jugular vein, a 3F pediatric radial artery catheter (model C-PUM-301J, Cook) was advanced into the right atrium. A precurved guide wire supplied with the catheter was then advanced through the catheter into the right ventricle until an endocardial ECG was observed. Through the right femoral artery, a Teflon catheter (UTX 022, Becton Dickinson) was advanced into the thoracic aorta for measurement of aortic pressure with a model TNF-R transducer (Abbott Critical Care). Through the left femoral artery and left femoral vein, catheters (UTX 022, Becton Dickinson) were advanced into the abdominal aorta and inferior vena cava for sampling arterial blood and blood replacement. Rectal temperature was measured continuously with a rectal thermistor. Conventional lead II ECGs were recorded with skin electrodes (model E220, In-vivo Metric).

Figure 1:
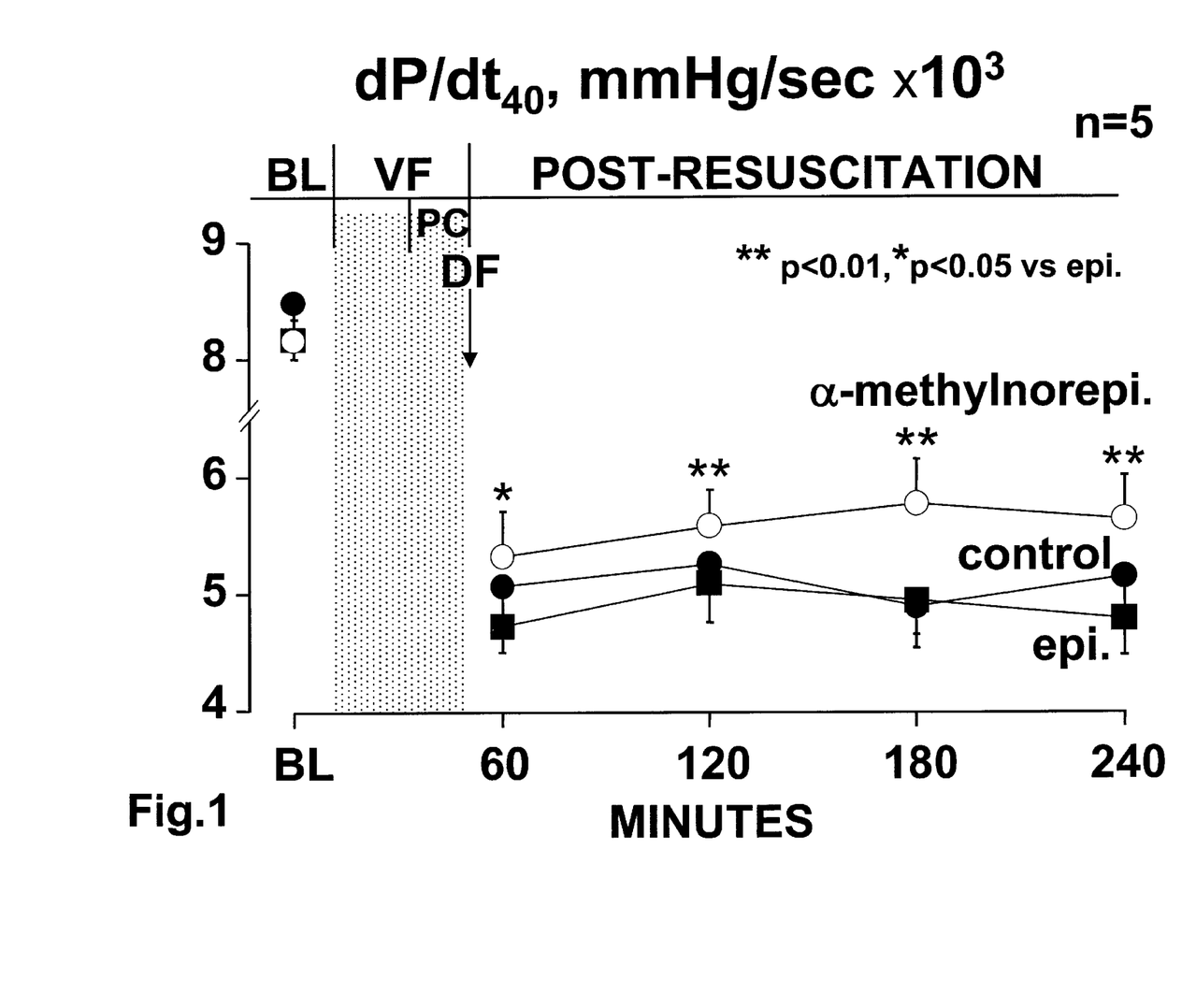
FIG. 1 is a graph illustrating the relative effects of epinephrine, α-methylnorepinephrine and a control (saline placebo) on post-resuscitation myocardial dysfunction as measured by dp/dt40, as described in Example 1.
Figure 2:
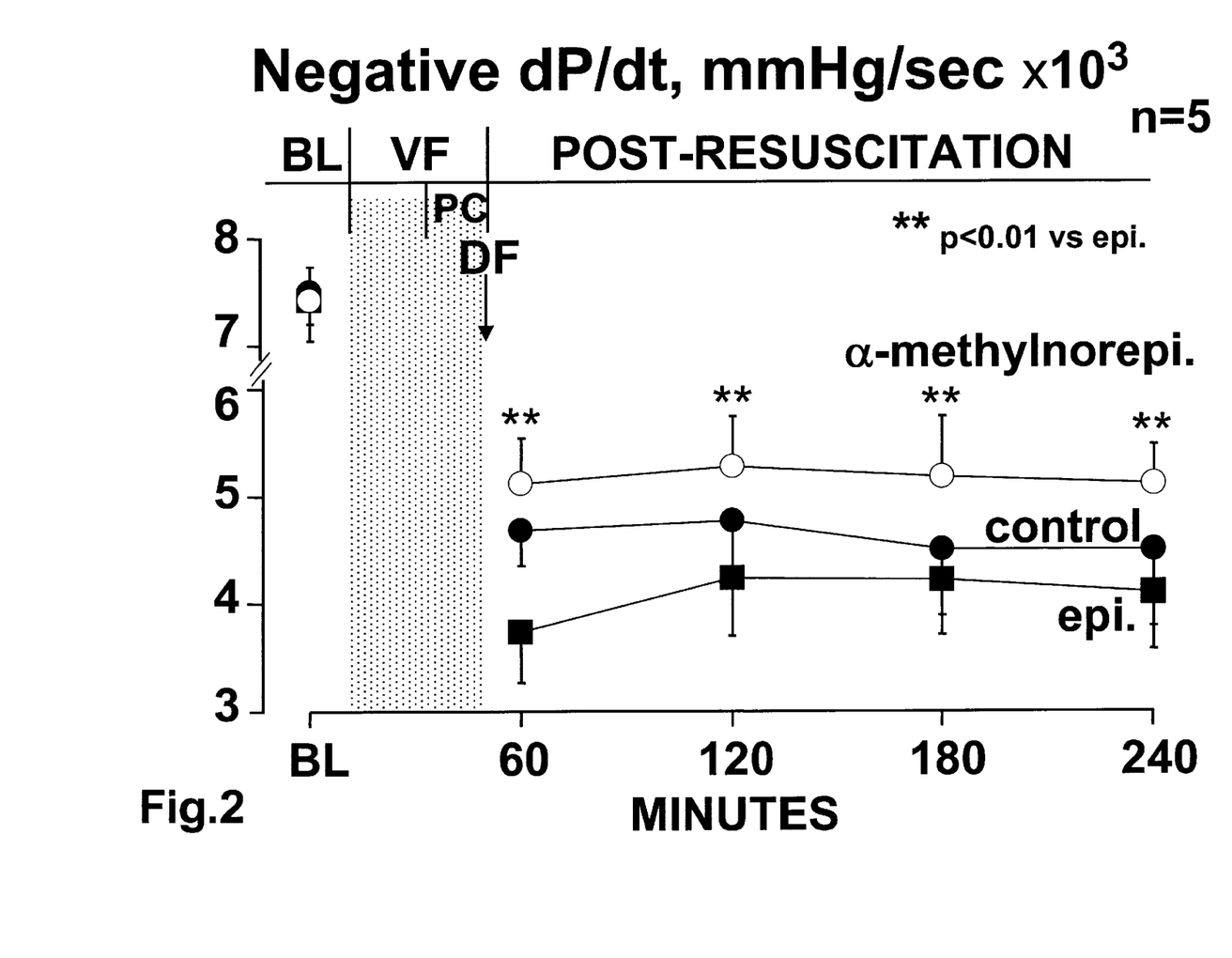
FIG. 2 is a graph illustrating the relative effects of epinephrine, α-methylnorepinephrine and a control (saline placebo) on post-resuscitation myocardial dysfunction as measured by negative dP/dt, also as described in Example 1.
Figure 3:
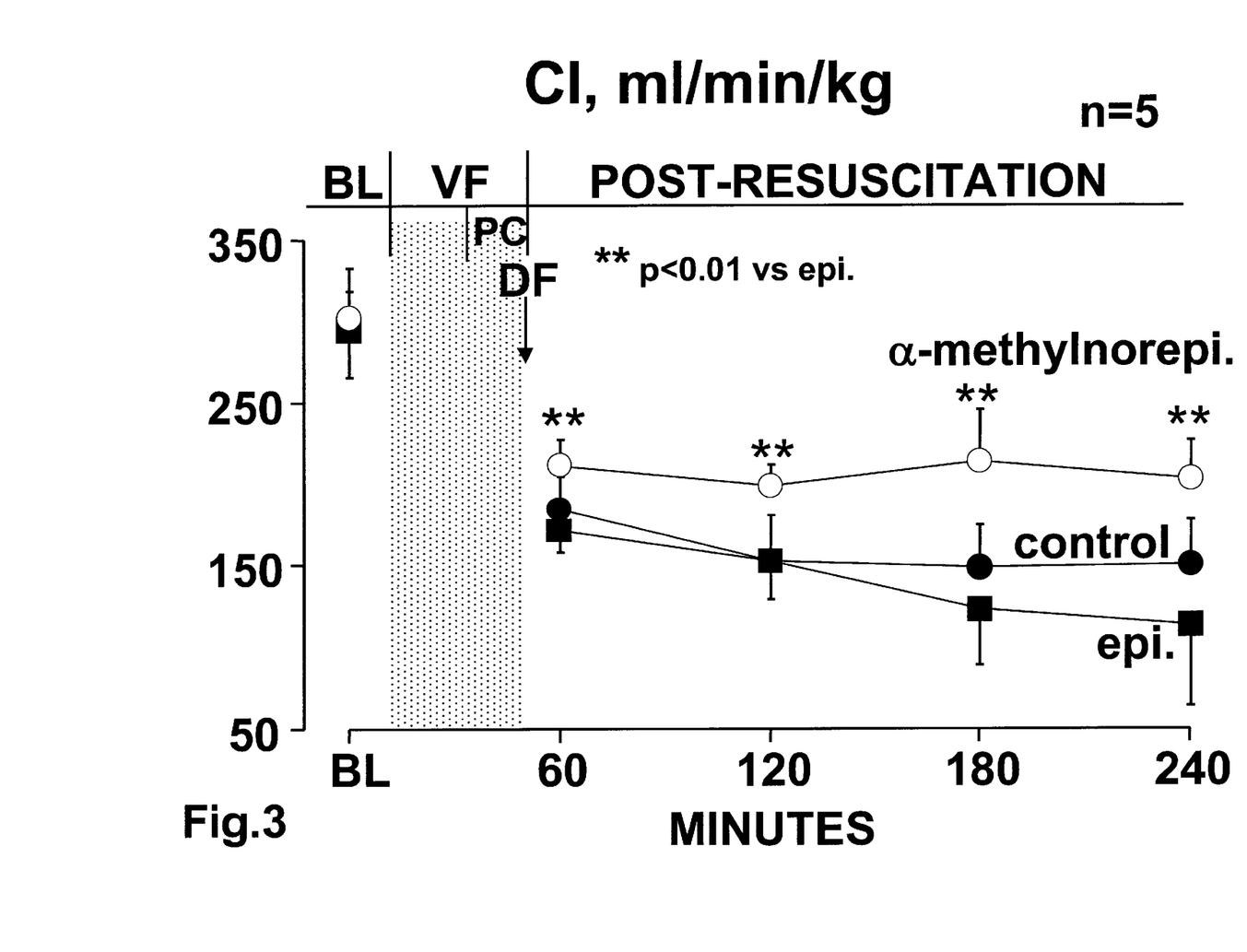
FIG. 3 is a graph illustrating the relative effects of epinephrine, α-methylnorepinephrine and a control (saline placebo) on post-resuscitation myocardial dysfunction as measured by cardiac index ("CI"; ml/min/kg), also as described in Example 1.
Figure 4:
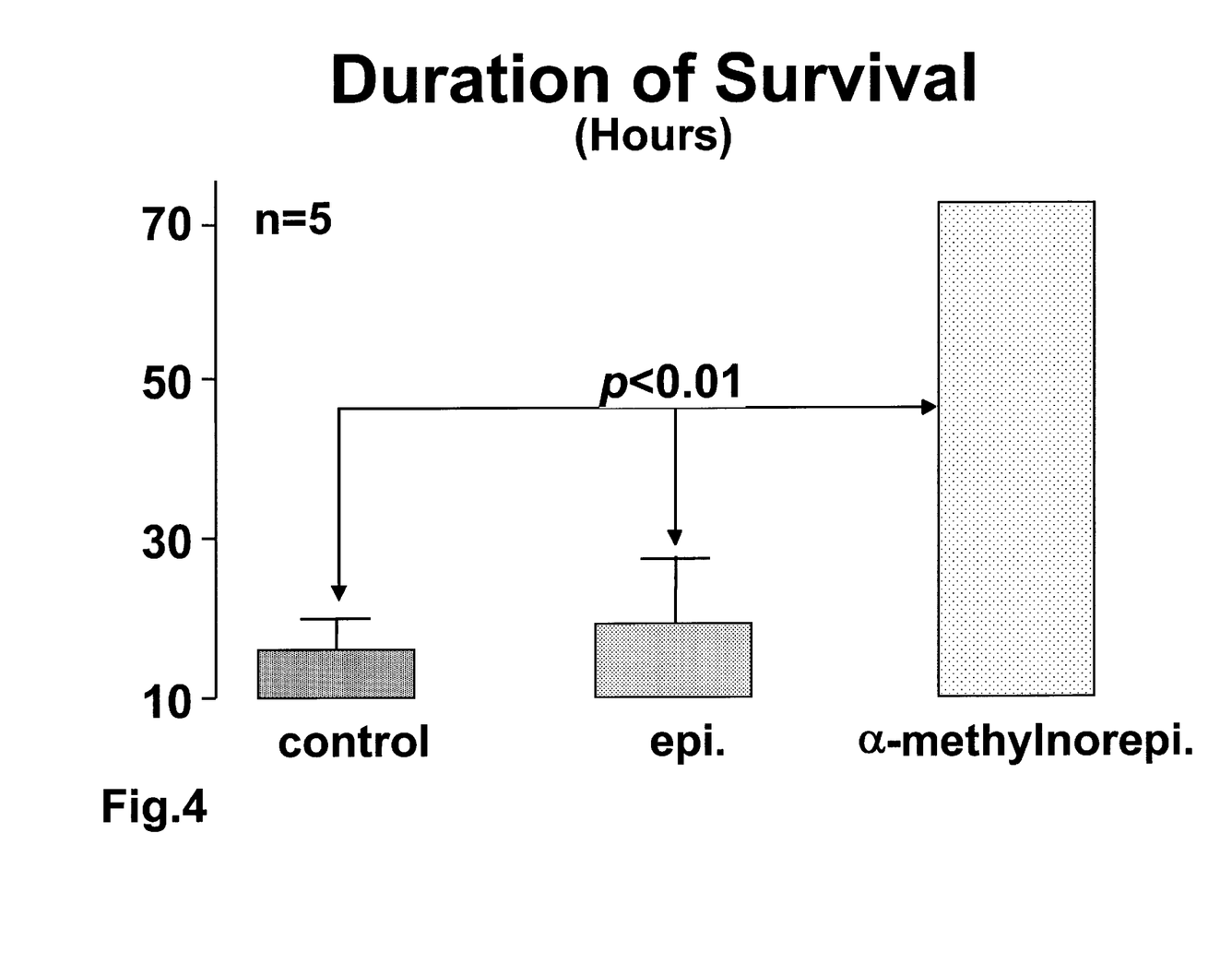
FIG. 4 is bar graph comparing the duration of post-resuscitation survival in animals receiving epinephrine, α-methylnorepinephrine and a control (saline placebo), also as described in Example 1.

Ventricular fibrillation (VF) was induced and untreated for 8 minutes. Precordial compression (PC) was then initiated. After 2 minutes of precordial compression, animals were randomized to receive either the selective $\alpha_2$-adrenergic agent, α-methylnorepinephrine (100 μg/kg; catalog number M133, Research Biochemicals International; abbreviated "α-methylnorepi."), epinephrine (30 μg/kg; abbreviated "epi.") or saline placebo. Defibrillation (DF) was attempted 4 min. later. All animals were successfully resuscitated. However, animals that received α-methylnorepinephrine demonstrated a significantly lower incidence of post-resuscitation ventricular arrhythmias. This was associated with significantly less severe post-resuscitation myocardial dysfunction as measured by dp/dt40 (FIG. 1), negative dP/dt (FIG. 2) and cardiac index (CI; FIG. 3). The duration of post-resuscitation survival was significantly greater in animals receiving α-methylnorepinephrine (72 hours) when compared with those receiving epinephrine (19 hours) and saline placebo (17 hours, FIG. 4). Baseline (BL) or control values are shown at the left of the figures.

EXAMPLE 2

Male domestic pigs weighing between 40 and 45 kg were fasted overnight except for free access to water. Anesthesia was initiated by intramuscular injection of ketamine (20 mg/kg) and completed by ear vein injection of sodium pentobarbital (30 mg/kg). Additional doses of sodium pentobarbital (8 mg/kg) were injected at intervals of 1 h to maintain anesthesia. A cuffed endotracheal tube was advanced into the trachea. Animals were mechanically ventilated with a volume-controlled ventilator (Model MA-1; Puritan-Bennett, Carlsbad, Calif.). End tidal $PCO_2$ ($P_{ET}CO_2$) was monitored with an infrared analyzer (Model 01R-7101A; Nihon Kohden Corp., Tokyo, Japan). Respiratory frequency was adjusted to maintain $P_{ET}CO_2$ between 35 and 40 mm Hg.

For the measurement of left ventricular function, a 5-MHZ single plane with 5 MHZ continuous-wave Doppler transesophageal echocardiographic transducer with four-way flexure (Model 21363A; Hewlett-Packard Co., Medical Products Group, Andover Mass.) was advanced from the incisor teeth into the esophagus for a distance of approximately 35 cm. For the measurement of aortic pressure, a fluid-filled catheter was advanced from the left femoral artery into the thoracic aorta. For the measurement of right atrial pressure, pulmonary arterial pressures and blood temperature, a 7-F, pentalumen, thermodilation-tip catheter was advanced from the left femoral vein and flow directed into the pulmonary artery. For inducing ventricular fibrillation (VF), a 5-F pacing catheter (EP Technologies, Inc., Mountain View, Calif.) was advanced from the right cephalic vein into the right ventricle until an electrocardiographic current of injury was recorded.

Figure 5:
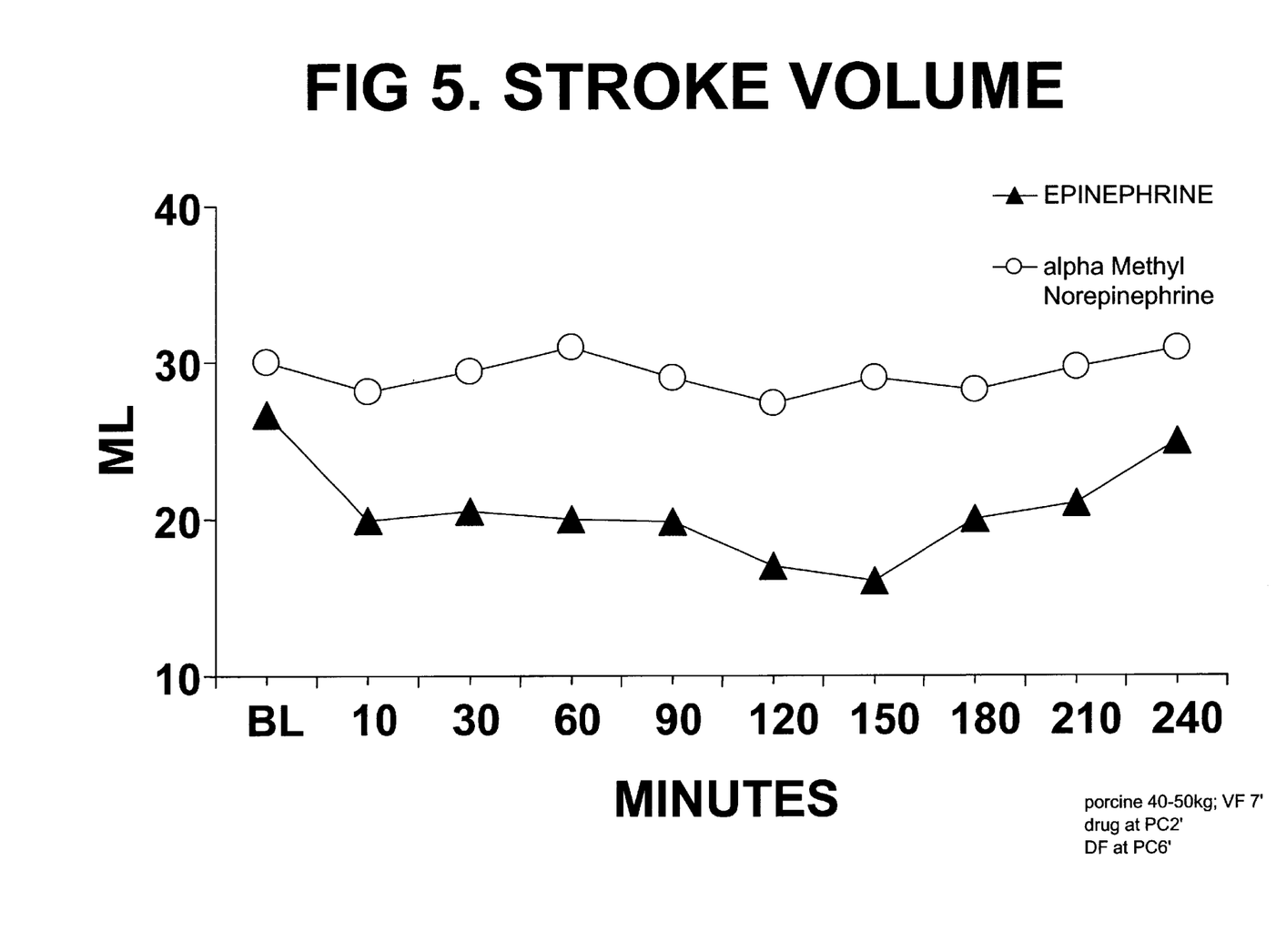
FIG. 5 is a graph illustrating the relative effects of epinephrine and α-methylnorepinephrine on post-resuscitation left ventricular stroke volume (ml/min) in pigs, using the protocol described in Example 2.
Figure 6:
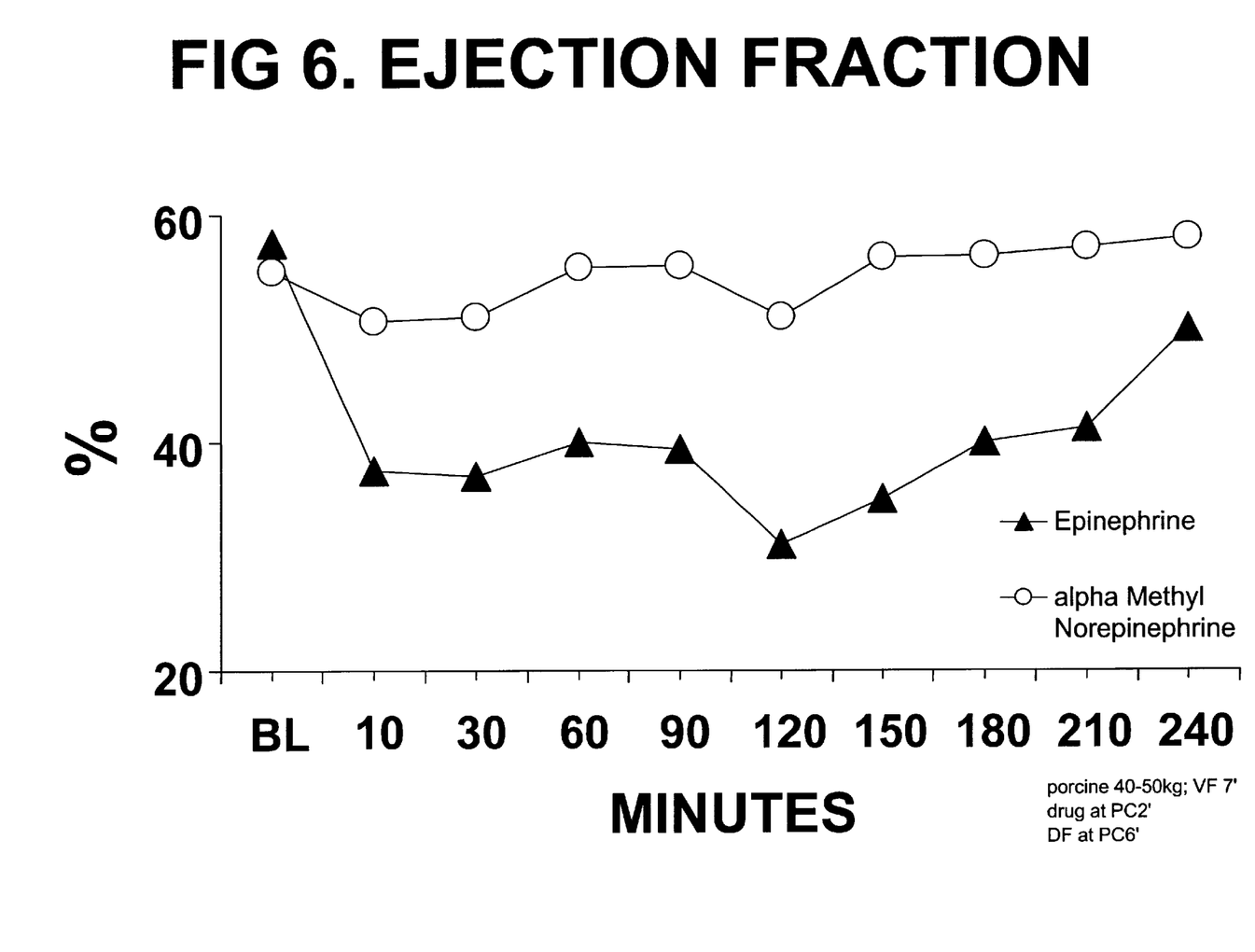
FIG. 6 is a graph illustrating the relative effects of epinephrine and α-methylnorepinephrine on ejection fraction, in pigs, using the protocol described in Example 2.
Figure 7:
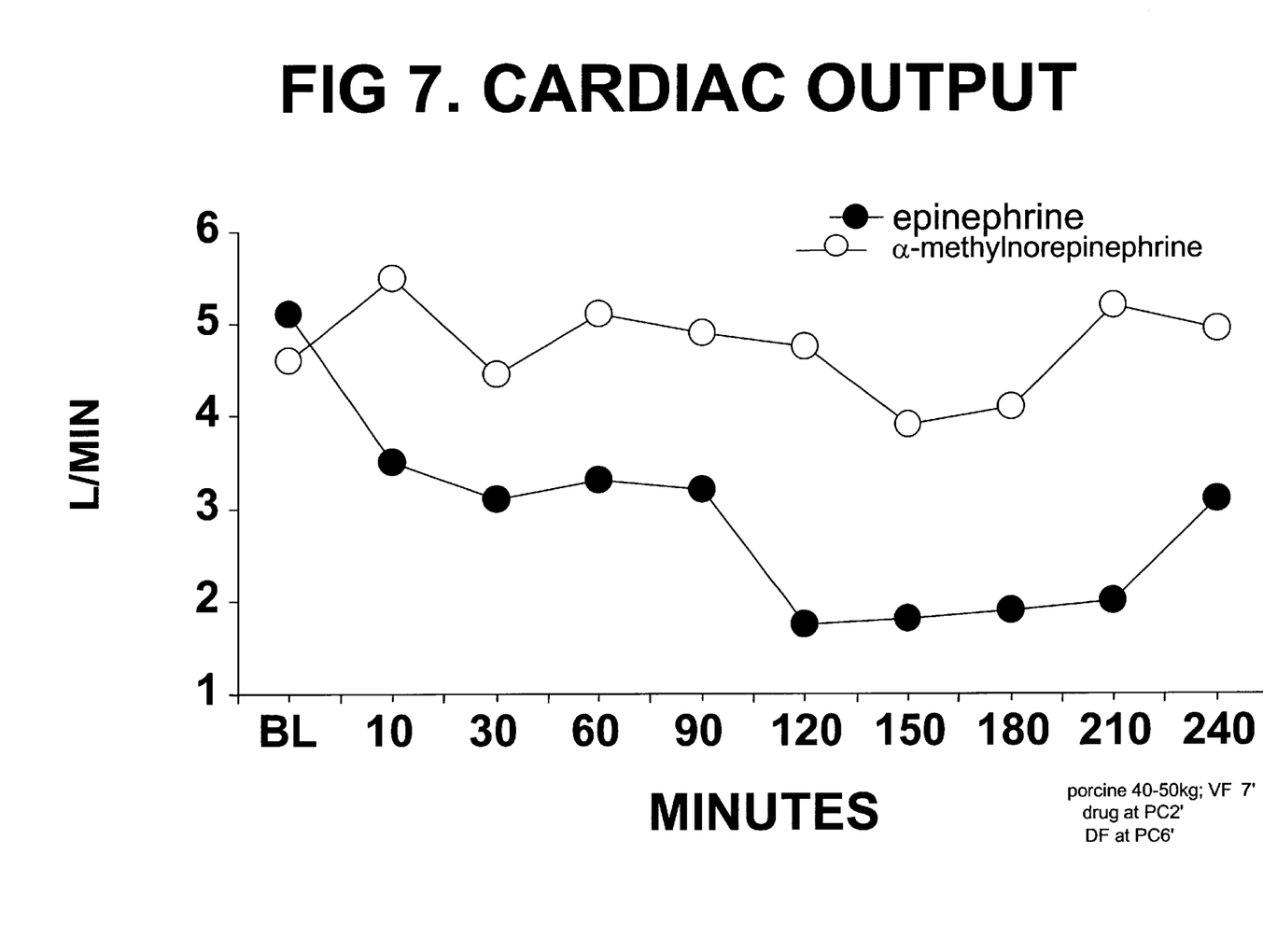
FIG. 7 is a graph illustrating the relative effects of epinephrine and α-methylnorepinephrine on cardiac output (liters/min), in pigs, using the protocol described in Example 2.

Ventricular fibrillation (VF) was induced and untreated for 7 minutes. Precordial compression (PC) was then initiated. After 2 minutes of precordial compression, animals were randomized to receive either the selective $\alpha_2$-adrenergic agent, α-methylnorepinephrine (100 μg/kg; catalog number M133, Research Biochemicals International) or epinephrine (30 μg/kg). Defibrillation was attempted 4 min. later. All animals were successfully resuscitated. A lower incidence of post-resuscitation ventricular arrhythmias was again observed with those animals receiving α-methylnorepinephrine. This was associated with markedly improved post-resuscitation left ventricular stroke volume (FIG. 5), ejection fraction (FIG. 6), and cardiac output (FIG. 7) as measured by transesophageal echo-Doppler methods.

What is claimed is:

1. A method for resuscitating a patient suffering from cardiac arrest, comprising the steps of:
    (a) actively inducing venous blood transport into the heart and arterial blood transport from the heart;
    (b) ventilating the patient's lungs;
    (c) administering to the patient concurrently with steps (a) and (b) a therapeutically effective amount of an active agent comprising an $\alpha_2$-receptor agonist that does not cross the blood brain barrier.

2. The method of claim 1, wherein the active agent is a selective $\alpha_2$-receptor agonist.

3. The method of claim 2, wherein the active agent is α-methylnorepinephrine.

4. The method of claim 3, wherein the therapeutically effective amount is in the range of approximately 10 µg/kg to 1.0 mg/kg.

5. The method of claim 4, wherein the therapeutically effective amount is in the range of approximately 10 µg/kg to 500 µg/kg.

6. The method of claim 4, wherein the therapeutically effective amount is in the range of approximately 50 µg/kg to 200 µg/kg.

7. The method of claim 1, wherein administration of the active agent is parenteral or endotracheal.

8. The method of claim 7, wherein administration is parenteral.

9. The method of claim 8, wherein administration is by intravenous injection.

10. The method of claim 9, wherein the intravenous injection is a bolus intravenous injection.

11. The method of claim 10, wherein the bolus intravenous injection is repeated at a rate of approximately once per 2 minutes to approximately once per 15 minutes.

12. The method of claim 7, wherein the active agent is administered endotracheally.

13. The method of claim 7, wherein the active agent is administered via an implanted reservoir.

14. The method of claim 1, wherein the active agent is administered in a pharmaceutical formulation comprising a pharmaceutically acceptable carrier.

15. The method of claim 14, wherein the formulation comprises an additional active agent.

16. The method of claim 15, wherein the additional active agent is an antiarrhythmic agent.

17. The method of claim 16, wherein the antiarrhythmic agent comprises a class I antiarrhythmic agent.

18. The method of claim 17, wherein the class I antiarrhythmic agent is selected from amiodarone, quinidine, procainamide, disopyramide, mixelitine, lidocaine, tocainide, phenytoin, flecainide, moricizine and propafenone.

19. The method of claim 16, wherein the antiarrhythmic agent comprises a class II antiarrhythmic agent.

20. The method of claim 19, wherein the class II antiarrhythmic agent is selected from propanolol, esmolol and sotalol.

21. The method of claim 16, wherein the antiarrhythmic agent comprises a class III antiarrhythmic agent.

22. The method of claim 21, wherein the class III antiarrhythmic agent is selected from bretylium and ibutilide.

23. The method of claim 16, wherein the antiarrhythmic agent comprises a class IV antiarrhythmic agent.

24. The method of claim 23, wherein the class IV antiarrhythmic agent is selected from verapamil, diltiazem and bepridil.

25. The method of claim 16, wherein the antiarrhythmic agent is selected from digoxin, edrophonium, adenosine, magnesium and potassium.

26. A method for enhancing the efficacy of cardiopulmonary resuscitation, comprising:

applying an electrical defibrillatory shock to a mammalian individual in cardiac arrest; and administering to the individual an active agent comprising an $\alpha_2$-receptor agonist that does not cross the blood brain barrier.

27. The method of claim 26, wherein the active agent is a selective $\alpha_2$-receptor agonist.

28. The method of claim 27, wherein the active agent is α-methylnorepinephrine.

29. The method of claim 28, wherein the therapeutically effective amount is in the range of approximately 10 µg/kg to 1.0 mg/kg.

30. The method of claim 28, wherein the therapeutically effective amount is in the range of approximately 10 µg/kg to 500 µg/kg.

31. The method of claim 28, wherein the therapeutically effective amount is in the range of approximately 50 µg/kg to 200 µg/kg.

32. A method for enhancing the efficacy of cardiopulmonary resuscitation (CPR), comprising administering to a patient during or subsequent to CPR a therapeutically effective amount of an active agent comprising an $\alpha_2$-receptor agonist that does not cross the blood-brain barrier.

33. The method of claim 32, wherein the active agent is a selective $\alpha_2$-receptor agonist.

34. The method of claim 33, wherein the active agent is α-methylnorepinephrine.

35. The method of claim 34, wherein the therapeutically effective amount is in the range of approximately 10 µg/kg to 1.0 mg/kg.

36. The method of claim 34, wherein the therapeutically effective amount is in the range of approximately 20 µg/kg to 500 µg/kg.

37. The method of claim 34, wherein the therapeutically effective amount is in the range of approximately 50 µg/kg to 200 µg/kg.

38. The method of claim 32, wherein the active agent is administered during CPR.

39. The method of claim 32, wherein the active agent is administered subsequent to CPR.

40. A method for treating myocardial dysfunction in a patient following cardiopulmonary resuscitation, comprising administering a therapeutically effective amount of an active agent comprising an $\alpha_2$-receptor agonist that does not cross the blood-brain barrier.

41. A method for treating post-resuscitation hypotension in a patient following cardiopulmonary resuscitation, comprising administering a therapeutically effective amount of an active agent comprising an $\alpha_2$-receptor agonist that does not cross the blood-brain barrier.

42. A method for reducing the incidence of ventricular arrhythmias in a patient following cardiopulmonary resuscitation, comprising administering a therapeutically effective amount of an active agent comprising an $\alpha_2$-receptor agonist that does not cross the blood-brain barrier.

43. A method for reducing the incidence of myocardial dysfunction in a patient following cardiopulmonary resuscitation, comprising administering a therapeutically effective amount of an active agent comprising an $\alpha_2$-receptor agonist that does not cross the blood-brain barrier.

* * * * *